United States Patent

Bennett et al.

[11] Patent Number: 5,939,191
[45] Date of Patent: Aug. 17, 1999

[54] COATED GUT SUTURE

[75] Inventors: Steven L. Bennett, Southington; Ying Jiang, North Haven; Mark S. Roby, Killingworth; Nagabhushanam Totakura, North Haven, all of Conn.

[73] Assignee: United States Surgical Corporation, Norwalk, Conn.

[21] Appl. No.: 08/880,303

[22] Filed: Jun. 23, 1997

Related U.S. Application Data

[63] Continuation of application No. 08/657,059, May 28, 1996, abandoned, which is a continuation of application No. 08/338,668, Nov. 14, 1994, abandoned, which is a continuation-in-part of application No. 08/075,995, Jun. 11, 1993, abandoned.

[51] Int. Cl.$^6$ ............................. B05D 1/36; A61B 17/04
[52] U.S. Cl. ..................... 428/375; 427/384; 427/407.1; 427/417; 428/378; 428/394; 528/354; 528/355; 606/230; 606/231
[58] Field of Search ................................ 427/407.1, 384, 427/417; 428/375, 378, 394; 528/354, 355; 606/230, 231

[56] References Cited

U.S. PATENT DOCUMENTS

| | | | |
|---|---|---|---|
| 1,239,690 | 9/1917 | Hollister . | |
| 2,128,701 | 8/1938 | Gelinsky | 128/335.5 |
| 2,394,054 | 2/1946 | Hall | 128/335.5 |
| 2,519,404 | 8/1950 | Rynkiewicz | 128/335.5 |
| 2,524,772 | 10/1950 | Davis et al. | 8/94.11 |
| 2,576,576 | 11/1951 | Cresswell et al. | 206/63.3 |
| 2,640,752 | 6/1953 | Davis et al. | 206/63.3 |
| 2,694,487 | 11/1954 | Pewers et al. | 206/63.3 |
| 3,166,073 | 1/1965 | Kronenthal | 128/335.5 |
| 3,413,079 | 11/1968 | Rich, Jr. | 8/130.1 |
| 3,478,140 | 11/1969 | Kronenthal et al. | 260/784 |
| 3,773,737 | 11/1973 | Goodman et al. | 128/335.5 |
| 3,896,814 | 7/1975 | Vivien et al. | 128/335 |
| 3,942,532 | 3/1976 | Hunter et al. | 128/335.5 |
| 4,027,676 | 6/1977 | Mattei | 128/335.5 |
| 4,105,034 | 8/1978 | Shalaby et al. | 128/335.5 |
| 4,185,637 | 1/1980 | Mattei | 128/335.5 |
| 4,190,720 | 2/1980 | Shalaby | 528/37 |
| 4,201,216 | 5/1980 | Mattei | 128/335.5 |
| 4,347,234 | 8/1982 | Wahlig et al. | 424/15 |
| 4,506,672 | 3/1985 | Bichon | 128/335.5 |
| 4,532,929 | 8/1985 | Mattei et al. | 128/335.5 |
| 4,605,730 | 8/1986 | Shalaby et al. | 528/357 |
| 4,624,256 | 11/1986 | Messier et al. | 128/335.5 |
| 4,649,920 | 3/1987 | Rhum | 128/335.5 |
| 4,700,704 | 10/1987 | Jamiolkowski et al. | 128/335.5 |
| 4,788,979 | 12/1988 | Jarrett et al. | 128/335.5 |
| 4,791,929 | 12/1988 | Jarrett et al. | 128/335.5 |
| 4,857,602 | 8/1989 | Casey et al. | 525/408 |
| 4,994,074 | 2/1991 | Bezwada et al. | 606/230 |
| 5,037,429 | 8/1991 | Hermes et al. | 606/230 |
| 5,076,807 | 12/1991 | Bezwada et al. | 606/230 |
| 5,080,665 | 1/1992 | Jarrett et al. | 606/219 |
| 5,085,629 | 2/1992 | Goldberg et al. | 604/8 |
| 5,100,433 | 3/1992 | Bezwada et al. | 528/354 |
| 5,104,398 | 4/1992 | Planck et al. | 606/230 |
| 5,210,108 | 5/1993 | Spinu et al. | 521/182 |
| 5,371,176 | 12/1994 | Bezwada et al. | 528/354 |

FOREIGN PATENT DOCUMENTS

| | | |
|---|---|---|
| 0117538 | 9/1984 | European Pat. Off. . |
| 0 128 043 | 12/1984 | European Pat. Off. . |
| 0409735 | 1/1991 | European Pat. Off. . |
| 0558965 | 9/1993 | European Pat. Off. . |
| 0 628 587 | 12/1994 | European Pat. Off. . |

*Primary Examiner*—D. S. Nakarani

[57] ABSTRACT

A gut suture is coated with a bioabsorbable copolymer obtained by polymerizing a major amount of ε-caprolactone and a minor amount of at least one other copolymerizable monomer in the presence of polyhydric alcohol as initiator. The coated gut suture can be packaged in the absence of conventional tubing fluid, i.e., in the dry state, while at the same time retaining flexibility, pliability and resistance to fray. In an alternative embodiment, a gut suture is coated with a pre-coating composition prior to being coated with the bioabsorbable copolymer.

16 Claims, 1 Drawing Sheet

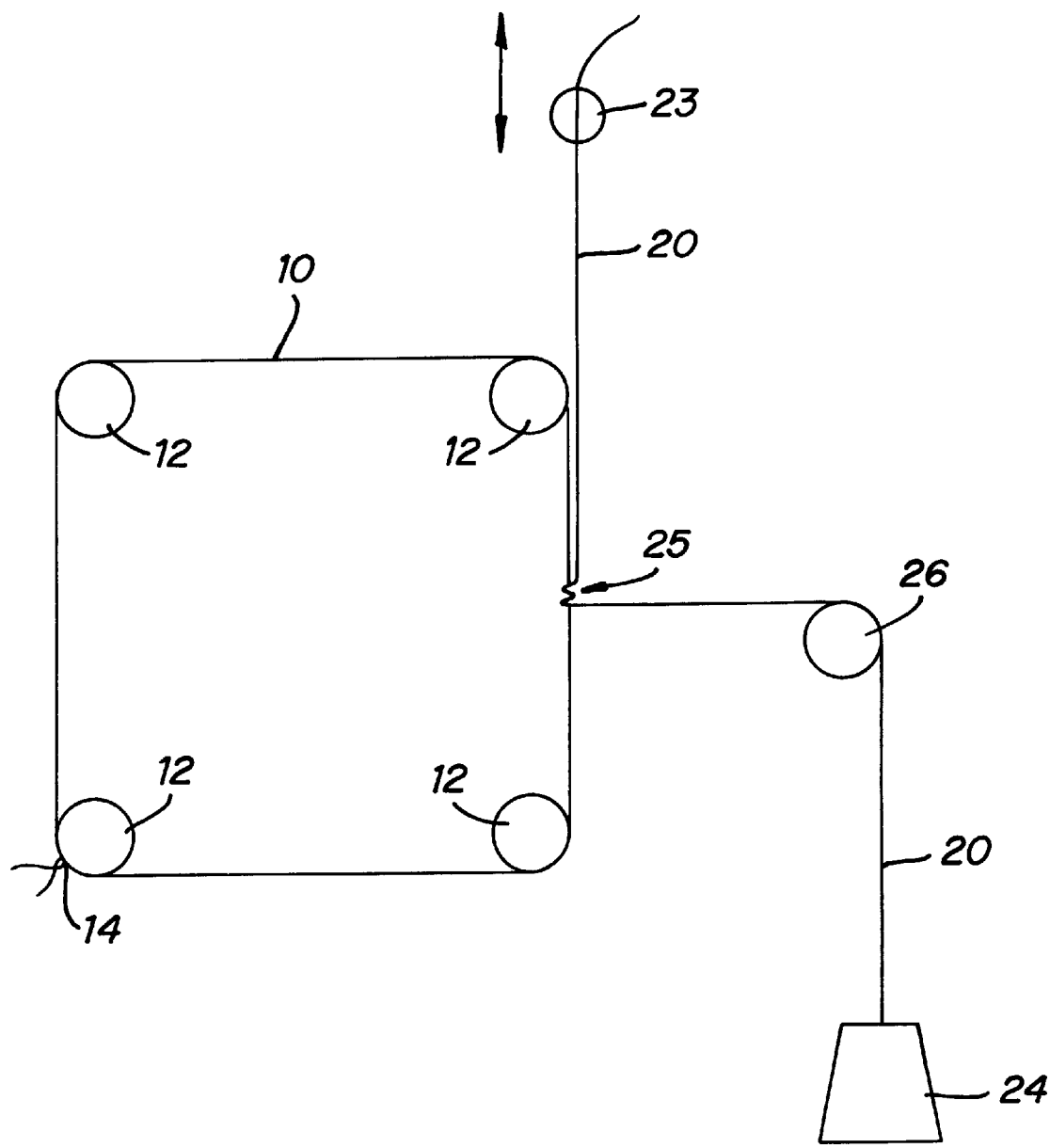
FIG_1

COATED GUT SUTURE

CROSS-REFERENCE TO RELATED APPLICATION

This is a continuation of U.S. application Ser. No. 08/657,059 filed on May 28, 1996, now abandoned, which is a continuation of U.S. application Ser. No. 08/338,668 filed on Nov. 14, 1994, now abandoned, which is a continuation-in-part of U.S. application Ser. No. 08/075,995 filed on Jun. 11, 1993, now abandoned.

BACKGROUND

1. Technical Field

The present disclosure relates to a coated gut suture and, more particularly, to a coated gut suture which is capable of being dry packaged.

2. Background of the Related Art

Absorbable sutures are manufactured from natural or synthetic materials. Some of the earliest absorbable sutures were made of collagenous material taken from sheep intestines. Such sutures are still in use today and are commonly referred to as "catgut" or simply "gut" sutures or ligatures. In the present specification, the term "catgut" or "gut" suture refers to a collagen based suture or ligature of any type or origin. Gut sutures may be prepared in the form of threads or strands that are undesirably stiff before subsequent treatment which renders them flexible or pliable.

A suture having a good degree of flexibility and pliability can conform closely to body tissue without undue pressure. Good flexibility and pliability enhance the degree to which a suture can be tied down, knotted and securely placed in a desired position.

Various attempts have been made to modify and optimize the physical characteristics of gut sutures. For example, tubing fluids, i.e., liquids which are used to condition gut sutures to achieve or enhance flexibility and pliability, have been used to preserve gut sutures. Tubing fluids typically contain an alcohol such as isopropyl alcohol and a relatively small percentage of water. Examples of tubing fluids are found in U.S. Pat. Nos. 1,239,690, 2,394,054, 2,519,404, 2,524,772, and 2,694,487. Ideally, the tubing fluid aids the gut suture to retain its flexibility and pliability without adversely affecting the strength and overall integrity of the suture.

Commercially available gut sutures are immersed in tubing fluid, sterilized and supplied to surgeons in packages or tubes which contain tubing fluid. The alcohol and water present in the tubing fluid keep the suture flexible and pliable as long as they remain in contact with the suture. As the tubing fluid evaporates, the suture loses its flexibility and pliability which may affect handling characteristics.

In addition to tubing fluids, various suture coatings which adhere to the surface of the suture have been developed in an attempt to maintain flexibility and control swelling and fraying. Such coatings are also intended to improve the handling characteristics of sutures and maximize run-down performance. For example, U.S. Pat. No. 3,942,532 discloses a suture coating composition obtained by polymerizing lactones such as ε-caprolactone in the presence of a polymethylenediol. U.S. Pat. No. 4,624,256 discloses a suture coating composition containing a high molecular weight ε-caprolactone homopolymer, or a copolymer derived from a major amount of ε-caprolactone and a minor amount of a comonomer or a blend of such an ε-caprolactone polymer with a lubricating agent (e.g., sterol esters of fatty acids).

Copolymers derived from ε-caprolactone and at least one other monomer such as glycolide, lactide, p-dioxanone and trimethylene carbonate are disclosed in U.S. Pat. Nos. 4,605,730, 4,624,256, 4,700,704, 4,788,979, 4,791,929, 4,994,074, 5,076,807, 5,080,665, 5,085,629 and 5,100,433.

U.S. Pat. No. 3,896,814 discloses a dry-packaged gut suture which is coated with a treatment agent such as polyoxyethylene glycol. U.S. Pat. No. 4,027,676 discloses a gut suture coated with a three-component coating composition. This patent discloses polyalkylene glycol as one ingredient of the three-component coating composition. U.S. Pat. No. 4,506,672 discloses a gut suture coated with a cured isocyanate-capped polyester which can be packaged either dry or in alcohol-containing wrappers. U.S. Pat. No. 4,649,920 discloses an absorbable surgical suture coated with a high molecular weight poly(alkylene oxide).

The aforementioned U.S. Pat. Nos. 3,896,814, 4,027,676, 4,506,672 and 4,649,920 do not disclose a gut suture which is coated with an ε-caprolactone-containing bioabsorbable copolymer.

SUMMARY

A gut suture is coated with a composition comprising a bioabsorbable copolymer obtained by polymerizing a major amount of ε-caprolactone and a minor amount of at least one other copolymerizable monomer in the presence of a polyhydric alcohol initiator.

The use of a polyhydric alcohol initiator, i.e., an alcohol possessing three or more hydroxyl groups, provides a copolymer having a branched, or "star", configuration. The branched structure of the bioabsorbable copolymer exerts a characteristic influence on its bioabsorption behavior making it useful as a coating material for gut sutures.

The gut suture coated with the bioabsorbable copolymer can optionally be packaged in the dry state, i.e., in the absence of tubing fluid, and yet still maintain substantially the same degree of flexibility, pliability and resistance to fray exhibited by a gut suture which is stored in tubing fluid. Thus, a gut suture coated with a coating composition in accordance with this disclosure can be packaged in a manner which is typical for conventional surgical sutures and, when removed from its package, be immediately employed by the surgeon.

In an alternative embodiment, a pre-coating composition is applied to the gut suture prior to being coated with a bioabsorbable copolymer in accordance with this disclosure. A preferred pre-coating composition includes poly(alkylene oxide) such as polyethylene glycol.

BRIEF DESCRIPTION OF THE DRAWING

FIG. 1 schematically illustrates a fray testing system for sutures.

DETAILED DESCRIPTION OF PREFERRED EMBODIMENTS

Conventional polymerization techniques that are well known and disclosed in the prior art can be utilized in preparing the bioabsorbable copolymer employed as a coating composition for a gut suture. The bioabsorbable copolymer is obtained by polymerizing a major amount of ε-caprolactone and a minor amount of at least one other copolymerizable monomer or mixture of such monomers in the presence of a polyhydric alcohol initiator. The polymerization of these monomers contemplates all of the various types of monomer addition, i.e., simultaneous, sequential, simultaneous followed by sequential, sequential followed by simultaneous, etc.

Suitable monomers which can be copolymerized with ε-caprolactone include glycolide, lactide, p-dioxanone and trimethylene carbonate.

Suitable polyhydric alcohol initiators include glycerol, trimethylolpropane, 1,2,4-butanetriol, 1,2,6-hexanetriol, triethanolamine, triisopropanolamine, erythritol, threitol, pentaerythritol, ribitol, arabinitol, xylitol, N,N,N',N'-tetrakis (2-hydroxyethyl)ethylenediamine, N,N,N',N'-tetrakis(2-hydroxypropyl)ethylenediamine, dipentaerythritol, allitol, dulcitol, glucitol, altritol, iditol, sorbitol, mannitol, inositol, and the like.

The copolymer can contain from about 70 to about 98, and preferably from about 80 to about 95, weight percent ε-caprolactone-derived units, the balance of the copolymer being derived from the other copolymerizable monomer(s). The inherent viscosity of the copolymer generally ranges from about 0.10 to about 0.60, and preferably from about 0.20 to about 0.50, dl/g when measured in chloroform at a concentration of 0.2500 g/dl at 30° C. The polyhydric alcohol initiator is generally employed in small amounts, e.g., from about 0.5 to about 5, and preferably from about 0.1 to about 2, weight percent of the total monomer mixture.

The bioabsorbable copolymer can be applied to a gut suture by any suitable process, e.g., by passing the gut suture through a solution of the copolymer, e.g., in acetone, methylene chloride, etc., past a brush or other coating solution applicator, or past one or more spray nozzles dispensing the gut suture coating solution. The gut suture wetted with the coating solution is subsequently air dried and/or passed through or held in a drying oven for a time and at a temperature sufficient to vaporize and drive off the solvent. Preferably, the coated gut suture is first air dried and then dried in an oven maintained at a temperature of about 50° C. The solution of bioabsorbable copolymer can contain a suitable amount of water or other moisturizing agent which swells the gut suture and imparts a desirable degree of flexibility and pliability to the suture. The bioabsorbable copolymer will entrap the moisture within the suture and/or enhance the retention of the moisture within the suture. If desired, the gut suture coating composition can optionally contain additional components, e.g., dyes, antibiotics, antiseptics, growth factors, anti-inflammatory agents, etc. The amount of coating composition applied to a gut suture will vary depending upon the structure of the suture, e.g., the number of filaments, tightness of braid or twist, the size of the suture and its composition.

In an alternative embodiment herein, a gut suture is pre-coated with a pre-coating composition prior to being coated with the bioabsorbable copolymer disclosed herein. Examples of pre-coating compositions which can be employed herein include compositions containing fatty acids, esters and ethers of fatty acids, polyalcohols, fatty alcohols, glycerine, glycols and derivatives thereof and poly(alkylene oxides). Pre-coating compositions containing poly(alkylene oxides) are preferred. Particularly preferred are poly(alkylene oxides) or derivatives thereof having molecular weights ranging from about 300 to about 5000. Examples of poly(alkylene oxides) which can be employed include polyethylene glycol, polypropylene glycol and polyethylene glycol methyl ether. Such pre-coating compositions can generally be applied to the gut suture at a level of from about 0.1 to about 10 weight percent or more and preferably from about 0.5 to about 5 weight percent, based on the final weight of the coated gut suture. The pre-coating composition can be applied to a gut suture by simply immersing the suture in a solution or suspension containing the pre-coating composition and drying the suture. The solution or suspension can contain water which swells the gut suture and becomes entrapped therein by virtue of the coating of the pre-coating composition. Optionally, the gut suture can be immersed in water and/or moisturizing agent to render the suture flexible and pliable prior to contacting the suture with the solution/suspension containing pre-coating composition.

The bioabsorbable copolymer can be applied to the suture after application of the pre-coating composition. The amount of bioabsorbable copolymer applied to a gut suture which has been pre-coated can range from about 0.2 to as much as about 3 weight percent or more and preferably from about 0.5 to about 2 weight percent. For a gut suture which has not been pre-coated, the bioabsorbable copolymer can be applied at a level of from about 0.5 to about 4 weight percent or more and preferably from about 1 to about 3 weight percent. As a practical matter, it is generally preferred to apply the minimum amount of coating composition consistent with good tie-down performance. This level of coating can be readily determined employing routine experimental procedures.

The following examples should be considered as illustrative and not as limitations of the present description. The examples demonstrate that coating formulations containing bioabsorbable copolymer and pre-coating composition as disclosed herein enhance the properties of gut sutures coated therewith.

Formulation 1

Dry glycolide (300 g), ε-caprolactone (2760 g), stannous octoate as catalyst (0.3 g) and dry mannitol as initiator (39.0 g) were mixed under $N_2$ for one hour. The mixture was heated in a reactor at a temperature of 160° C. for 24 hours. A solution of the resultant copolymer was prepared by dissolving the copolymer (5 g) in toluene (95 cc) and stirring the resultant mixture.

Formulation 2

A solution of polyethylene glycol methyl ether 350 (PEGME 350) (number average molecular weight of 350 and viscosity of 4.1 centistokes at 210° F.) was prepared by mixing PEGME 350 (50 cc) in isopropyl alcohol (50 cc) and stirring the resultant mixture.

Formulation 3

A solution of polyethylene glycol methyl ether 350 was prepared by mixing PEGME 350 (as used in Formulation 2) (70 cc) in isopropyl alcohol (30 cc) and stirring the resultant mixture.

Formulation 4

A solution of polyethylene glycol methyl ether 350 was prepared by mixing 60 cc of PEGME 350 (as used in Formulation 2) with 40 cc of a solution made from 20% water and 80% isopropyl alcohol.

Formulation 5

A solution of polyethylene glycol 600 (PEG 600) (number average molecular weight of 600 and viscosity of 10.5 centistokes at 210° F.) was prepared by mixing 60 cc of PEG 600 in 40 cc of a solution made from 20% water and 80% isopropyl alcohol.

EXAMPLE 1

Chrome gut sutures of size 1 are passed through a 10% solution of the copolymer of Formulation 1 in methylene chloride. The sutures are then air dried to remove the solvent, leaving a coating of the copolymer on the suture.

EXAMPLE 2

A chrome size 1 gut suture was dipped in the solution of Formulation 2 for 30 minutes, air dried and thereafter dried in an oven at 50° C. for 5 minutes. The suture was then dipped in the solution of Formulation 1 for about 1 minute, air dried for 120 minutes and oven-dried at 50° C. for 5 minutes. The resulting suture was then packaged dry and tested for number of cycles to break.

EXAMPLE 3

A chrome size 1 gut suture was dipped in the solution of Formulation 3 for 30 minutes, air dried and thereafter dried in an oven at 50° C. for 5 minutes. The suture was then dipped in the solution of Formulation 1 for about 1 minute, air dried for 120 minutes and oven-dried at 50° C. for 5 minutes. The resulting suture was then packaged dry and tested for number cycles to break.

EXAMPLE 4

A chrome size 1 gut suture was immersed in the solution of Formulation 4 for 30 minutes at 50° C., air dried for 60 minutes and thereafter immersed in the solution of Formulation 1 for about 1 minute. The suture was then removed, air dried for 120 minutes and oven-dried at 50° C. for 5 minutes. The resulting suture was then packaged dry and tested for number of cycles to break.

EXAMPLE 5

A chrome size 1 gut suture was immersed in the solution of Formulation 5 for 30 minutes at 50° C., air dried for 60 minutes and thereafter immersed in the solution of Formulation 1 for about 1 minute. The suture was removed, air dried for 120 minutes and oven-dried at 50° C. for 5 minutes. The resulting suture was then packaged dry and tested for number of cycles to break.

COMPARATIVE EXAMPLE 1

A chrome size 1 gut suture was immersed in isopropyl alcohol for 30 minutes at 50° C., air dried for 60 minutes and thereafter immersed in toluene for one minute. The coated suture was removed, air dried for 120 minutes and oven-dried at 50° C. for 5 minutes. Thus, this gut suture contains no polymeric coating composition. The suture was packaged dry and tested for number of cycles to break.

Table I below presents the data which resulted from tests conducted on the coated gut sutures of Examples 2–5 and Comparative Example 1. Tensile strength was tested in accordance with the test procedure described in ASTM D-2256. Percent elongation was tested in accordance with the test procedure described in ASTM D-2256. Young's Modulus, which is a measurement of flexibility, is the initial modulus as determined from the slope of the stress-strain curves produced in straight-pull strength tests carried out in accordance with the test procedure described in ASTM D-2256. Young's Modulus is the ratio of applied stress to strain in the elastic region.

TABLE I

| Example | Number of Cycles to Break | Standard Deviation | Tensile Strength (kpsi) | Percent Elongation | Young's Modulus (kpsi) |
|---|---|---|---|---|---|
| 2 | 52.7 | 11.0 | 75 | 21.3 | 178 |
| 3 | 28.4 | 34.0 | 76 | 21 | 89.7 |
| 4 | 17.7 | 13.0 | 83 | 20.5 | 208 |
| 5 | 44.5 | 12.0 | 81 | 21.6 | 207 |
| Comparative Example 1 | 0.3 | 0.2 | 79.2 | 18.9 | 199.7 |

The number of cycles needed to break each of the sutures of Examples 2–5 and Comparative Example 1 was determined using the fray resistance test schematically illustrated in FIG. 1. A static suture 10 is wound around rollers 12 and tied into a knot 14. A dynamic suture 20 is placed into a grip 23 and extended to reach the static suture 10 where it is wrapped twice at point 25 around the static suture 10. The dynamic suture 20 is extended around roller 26 and attached to a weight 24 which supplies tension to the dynamic suture 20. The grip 23 and dynamic suture 20 move up and down to cause the sutures to rub against each other at point 25. One cycle is a complete up and down movement of the grip 23 and dynamic suture 20. Testing conditions included a preload weight which is 15% of the USP limit on average knot pull strength for gut sutures. The travel distance for the grip was 50 mm for each cycle at a speed of 500 mm/minute. The test is dependent on the number of cycles needed to break a suture due to the fraying which occurs when one strand of suture, under applied load, slides against another static strand. A modified Sintech 1/G MTS system tester is used to conduct the fraying test. The bottom grip is removed from the tester, the load calibrated and gage set to zero. The static suture 10 is tied with sufficient tension around the rollers 12 of the fixture, forming a square. The fixture is adjusted so the point 25 where the static suture 10 and dynamic suture 20 interface is in line with the center line of the upper grip. The preload weight for these examples was 0.550 (15% of USP knot pull, kg.). The test is initiated with cycling observed until one of the sutures breaks to stop the test. If strands should lock themselves in a knot and do not slide against each other it is considered a break. The average number of cycles $(X_{ave.})$ is $X_{ave.}=(X_1+X_2+\ldots+X_n)/n$ wherein $X_n$ is the number of cycles to break each pair of strands and n is the number of pairs. The standard deviation $\overline{S}$ is calculated as $$\overline{S} = \sqrt{\frac{\sum (x_1 - x)^2}{n-1}}.$$

It can clearly be seen from the data of Table I that the average number of cycles to break the dry packaged gut sutures coated in accordance with this disclosure (Examples 2–5) were much higher relative to the uncoated dry packaged gut suture of Comparative Example 1. Furthermore, it can be seen from these data that the tensile strength, percent elongation and Young's modulus of each of the dry packaged coated sutures of Examples 2–5 remained comparable to that of the uncoated dry packaged suture of Comparative Example 1.

It will be understood that various modifications may be made to the embodiments disclosed herein. For example, the pre-coating composition can be applied to a gut suture after the bioabsorbable copolymer described herein has been applied to the suture. Therefore, the above description should not be construed as limiting, but merely as exemplifications within the scope and spirit of the claims appended hereto.

What is claimed is:

1. A gut suture coated with a coating composition comprising a bioabsorbable copolymer, the bioabsorbable copolymer consisting essentially of from about 70 to about 98 weight percent epsiloncaprolactone copolymerized with one or more monomers selected from the group consisting of glycolide, lactide, p-dioxanone and trimethylene carbonate, the bioabsorbable copolymer being polymerized in the presence of a polyhydric alcohol.

2. The gut suture of claim 1 wherein the polyhydric alcohol initiator is selected from the group consisting of glycerol, trimethylolpropane, 1,2,4-butanetriol, 1,2,6-hexanetriol, triethanolamine, triisopropanolamine, erythritol, threitol, pentaerythritol, ribitol, arabinitol, xylitol, N,N,N',N'-tetrakis(2-hydroxyethyl)ethylenediamine, N,N,N',N'-tetrakis(2-hydroxypropyl)ethylenediamine, dipentaerythritol, allitol, dulcitol, glucitol, altritol, iditol, sorbitol, mannitol and inositol.

3. The gut suture of claim 1 wherein the copolymer contains from about 80 to about 95 weight percent ε-caprolactone, the balance of the copolymer being derived from the other copolymerizable monomer(s).

4. The gut suture of claim 1 wherein the copolymer possesses an inherent viscosity of from about 0.10 to about 0.60 dl/g when measured in chloroform at a concentration of 0.2500 g/dl at 30° C.

5. The gut suture of claim 1 wherein the copolymer possesses a inherent viscosity of from about 0.20 to about 0.50 dl/g when measured in chloroform at a concentration of 0.2500 dl/g at 30° C.

6. The gut suture of claim 1 wherein the polyhydric alcohol initiator is employed in an amount of from about 0.5 to about 5 weight percent of the total monomer mixture.

7. The gut suture of claim 1 wherein the polyhydric alcohol initiator is employed in an amount of from about 0.1 to about 2 weight percent of the total monomer mixture.

8. The gut suture of claim 1 wherein the coating composition is applied to a gut suture at a level of from about 0.2 to about 4 weight percent of the entire coated suture.

9. The gut suture of claim 1 wherein the coating composition is applied to a gut suture at a level of from about 0.5 to about 3 weight percent of the entire coated suture.

10. The gut suture of claim 1 wherein the suture is dry packaged.

11. The gut suture of claim 1 wherein the suture is precoated with a pre-coating composition comprising fatty acids, esters and ethers of fatty acids, polyalcohols, fatty alcohols, glycerine, glycols and poly(alkylene oxides) prior to application of the coating composition.

12. The gut suture of claim 11 wherein the pre-coating composition comprises a poly(alkylene oxide) selected from the group consisting of polyethylene glycol, polypropylene glycol and polyethylene glycol methyl ether.

13. The gut suture of claim 11 wherein the suture is dry packaged.

14. A method of coating a gut suture which comprises:

a) applying a solution of bioabsorbable copolymer, the copolymer consisting essentially of from about 70 to about 98 weight percent ε-caprolactone copolymerized with one or more monomers selected from the group consisting of glycolide, lactide, p-dioxanone and trimethylene carbonate, the copolymer being polymerized in the presence of polyhydric alcohol to a gut suture; and b) drying the gut suture to provide a gut suture coated with the bioabsorbable copolymer.

15. The method of claim 14 further comprising the step of applying a pre-coating composition containing fatty acids, polyalcohols, fatty alcohols, glycerine, glycols and poly(alkylene oxides) to the gut suture prior to the step of applying a solution of bioabsorbable copolymer.

16. The method of claim 15 wherein the pre-coating composition comprises poly(alkylene oxide).

* * * * *